US008968404B2

(12) United States Patent
Dee

(10) Patent No.: US 8,968,404 B2
(45) Date of Patent: Mar. 3, 2015

(54) METHOD AND DEVICE FOR AMELIORATING JOINT CONDITIONS AND DISEASES

(75) Inventor: Derek Dee, Rancho Palos Verdes, CA (US)

(73) Assignee: Subchondral Solutions, Inc., Los Gatos, CA (US)

( * ) Notice: Subject to any disclaimer, the term of this patent is extended or adjusted under 35 U.S.C. 154(b) by 350 days.

(21) Appl. No.: 13/421,792

(22) Filed: Mar. 15, 2012

(65) Prior Publication Data

US 2012/0172880 A1  Jul. 5, 2012

Related U.S. Application Data

(63) Continuation-in-part of application No. 12/328,493, filed on Dec. 4, 2008, now abandoned.

(51) Int. Cl.
*A61F 2/38* (2006.01)
*A61F 2/30* (2006.01)
*A61F 2/28* (2006.01)

(52) U.S. Cl.
CPC ............... *A61F 2/30756* (2013.01); *A61F 2/38* (2013.01); *A61F 2002/2825* (2013.01); *A61F 2002/2892* (2013.01); *A61F 2002/3895* (2013.01)
USPC .................... 623/14.12; 623/18.11; 606/86 R

(58) Field of Classification Search
USPC ...................... 623/14.12, 16.11, 18.11, 17.16; 606/302
See application file for complete search history.

(56) References Cited

U.S. PATENT DOCUMENTS

| 4,055,862 A | 11/1977 | Farling et al. |
| 4,344,193 A | 8/1982 | Kenny |
| 4,502,161 A | 3/1985 | Wall |

(Continued)

FOREIGN PATENT DOCUMENTS

| EP | 0739631 B1 | 3/2003 |
| EP | 1719532 A3 | 7/2011 |

(Continued)

OTHER PUBLICATIONS

Dee, Derek, Written Opinion and International Search Report issued in related International Patent Application No. PCT/US2012/29291 on Jul. 13, 2012.

(Continued)

*Primary Examiner* — Thomas J Sweet
*Assistant Examiner* — Megan Wolf
(74) *Attorney, Agent, or Firm* — Kilpatrick Townsend and Stockton LLP

(57) ABSTRACT

A device for ameliorating joint conditions and diseases comprising a) a first section comprising a joint-ward end, an opposing mating end, and a lateral wall, a peripheral column partially forming the lateral wall of the first section, a central column, and three or more than three struts extending between and connecting the peripheral column and the central column, and each strut thereby supporting the central column, the joint-ward end further comprising a plurality of fenestrations formed by a confluence of the peripheral column, the central column and two adjacent struts of the three or more than three struts, and first section further comprising a central aperture within and formed by the central column, and configured to mate with a driver, b) a second section comprising a mating end, an opposing leading end, and a lateral wall, the lateral wall of the second section comprising threads.

14 Claims, 19 Drawing Sheets

(56) References Cited

U.S. PATENT DOCUMENTS

| | | | |
|---|---|---|---|
| 4,654,314 A | 3/1987 | Takagi et al. |
| 4,687,675 A | 8/1987 | Nakano et al. |
| 4,728,332 A | 3/1988 | Albrektsson |
| 4,880,429 A | 11/1989 | Stone et al. |
| 4,919,667 A | 4/1990 | Richmond |
| 4,963,145 A | 10/1990 | Takagi et al. |
| 5,007,934 A | 4/1991 | Stone et al. |
| 5,026,373 A | 6/1991 | Ray et al. |
| 5,171,322 A | 12/1992 | Kenny |
| 5,306,311 A | 4/1994 | Stone et al. |
| 5,344,459 A | 9/1994 | Swartz |
| 5,865,849 A | 2/1999 | Stone |
| 6,037,519 A | 3/2000 | McKay |
| 6,042,610 A | 3/2000 | Li et al. |
| 6,046,379 A | 4/2000 | Stone et al. |
| 6,093,204 A | 7/2000 | Stone |
| 6,149,651 A | 11/2000 | Drewry et al. |
| 6,193,755 B1 | 2/2001 | Metz-Stavenhagen et al. |
| 6,206,927 B1 | 3/2001 | Fell et al. |
| D450,122 S | 11/2001 | Michelson |
| 6,520,964 B2 * | 2/2003 | Tallarida et al. ................ 606/71 |
| 6,540,786 B2 | 4/2003 | Chibrac et al. |
| 6,629,997 B2 | 10/2003 | Mansmann |
| 6,645,251 B2 | 11/2003 | Salehi et al. |
| 6,699,252 B2 | 3/2004 | Farr, II et al. |
| 6,712,822 B2 * | 3/2004 | Re et al. ................ 606/75 |
| 6,758,865 B1 | 7/2004 | Stone et al. |
| 6,761,739 B2 | 7/2004 | Shepard |
| 6,783,550 B2 | 8/2004 | MacArthur |
| 6,793,676 B2 | 9/2004 | Plouhar et al. |
| 6,855,165 B2 | 2/2005 | Fell |
| 6,911,044 B2 | 6/2005 | Fell |
| 6,923,831 B2 | 8/2005 | Fell et al. |
| 6,994,730 B2 | 2/2006 | Posner |
| 7,066,961 B2 | 6/2006 | Michelson |
| 7,282,063 B2 | 10/2007 | Cohen et al. |
| 7,291,169 B2 | 11/2007 | Hodorek |
| 7,297,161 B2 | 11/2007 | Fell |
| 7,338,524 B2 | 3/2008 | Fell et al. |
| 7,608,105 B2 | 10/2009 | Pavlov et al. |
| 8,480,757 B2 | 7/2013 | Gage et al. |
| 8,591,592 B2 * | 11/2013 | Dreyfuss .............. 623/19.14 |
| 2002/0173855 A1 | 11/2002 | Mansmann |
| 2003/0040798 A1 | 2/2003 | Michelson |
| 2003/0109928 A1 | 6/2003 | Pasquet et al. |
| 2004/0006393 A1 | 1/2004 | Burkinshaw |
| 2004/0133275 A1 | 7/2004 | Mansmann |
| 2004/0199250 A1 | 10/2004 | Fell |
| 2004/0243250 A1 | 12/2004 | Stone et al. |
| 2005/0004572 A1 | 1/2005 | Biedermann et al. |
| 2005/0033424 A1 | 2/2005 | Fell |
| 2005/0043813 A1 | 2/2005 | Kusanagi et al. |
| 2005/0055101 A1 | 3/2005 | Sifneos |
| 2005/0060037 A1 | 3/2005 | Michelson |
| 2005/0171604 A1 | 8/2005 | Michalow |
| 2005/0209703 A1 | 9/2005 | Fell |
| 2005/0221703 A1 | 10/2005 | Stone |
| 2005/0234549 A1 | 10/2005 | Kladakis et al. |
| 2005/0267584 A1 | 12/2005 | Burdulis et al. |
| 2005/0278025 A1 | 12/2005 | Ku et al. |
| 2006/0173542 A1 | 8/2006 | Shikinami |
| 2006/0190078 A1 | 8/2006 | Fell |
| 2006/0224244 A1 | 10/2006 | Thomas et al. |
| 2007/0005143 A1 | 1/2007 | Ek et al. |
| 2007/0179610 A1 | 8/2007 | Biedermann et al. |
| 2008/0077248 A1 | 3/2008 | Murillo et al. |
| 2008/0249577 A1 * | 10/2008 | Dreyfuss ................ 606/308 |
| 2009/0024229 A1 | 1/2009 | Chen et al. |
| 2010/0145451 A1 | 6/2010 | Dee |
| 2011/0029081 A1 | 2/2011 | Malone |
| 2011/0125264 A1 | 5/2011 | Bagga et al. |
| 2012/0185044 A1 | 7/2012 | Dee |
| 2013/0035764 A1 | 2/2013 | Sharkey et al. |

FOREIGN PATENT DOCUMENTS

| | | |
|---|---|---|
| EP | 2174674 B1 | 1/2012 |
| EP | 2308027 B1 | 4/2013 |
| RU | 2146503 C1 | 3/2000 |
| RU | 2161929 C1 | 1/2001 |
| WO | 98/41246 A2 | 9/1998 |
| WO | 03/007879 A2 | 1/2003 |
| WO | 2010/065426 A2 | 6/2010 |
| WO | 2013/137889 A1 | 9/2013 |

OTHER PUBLICATIONS

International Search Report and Written Opinion of Application No. PCT/US2009/065993, Aug. 13, 2010, 15 pages.

Dee, Derek, Office Action dated Apr. 7, 2011 issued in related U.S. Appl. No. 12/328,493, filed Dec. 4, 2008.

Dee, Derek, Office Action dated Sep. 16, 2011 issued in related U.S. Appl. No. 12/328,493, filed Dec. 4, 2008.

Dee, Derek, Office Action dated Nov. 30, 2011 issued in related U.S. Appl. No. 12/328,493, filed Dec. 4, 2008.

Dee, Derek, PCT Patent Application No. PCT/US2012/029291 filed Mar. 15, 2012.

* cited by examiner

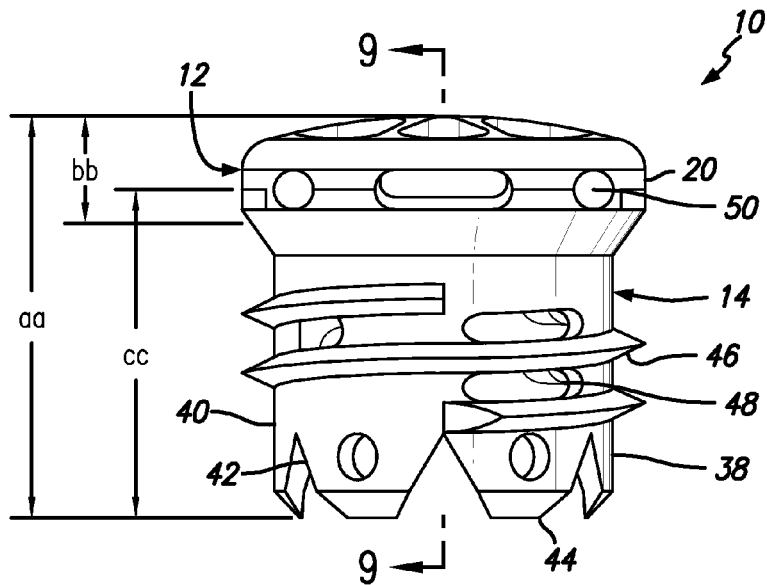
FIG. 1
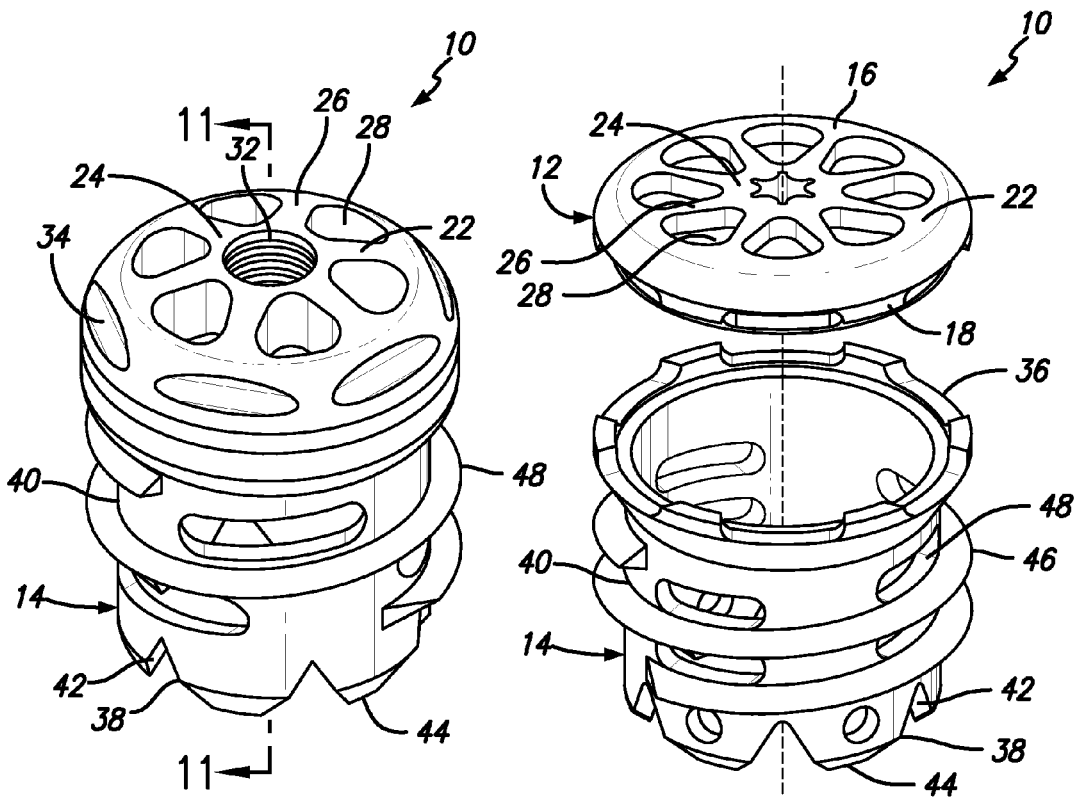
FIG. 2
FIG. 3

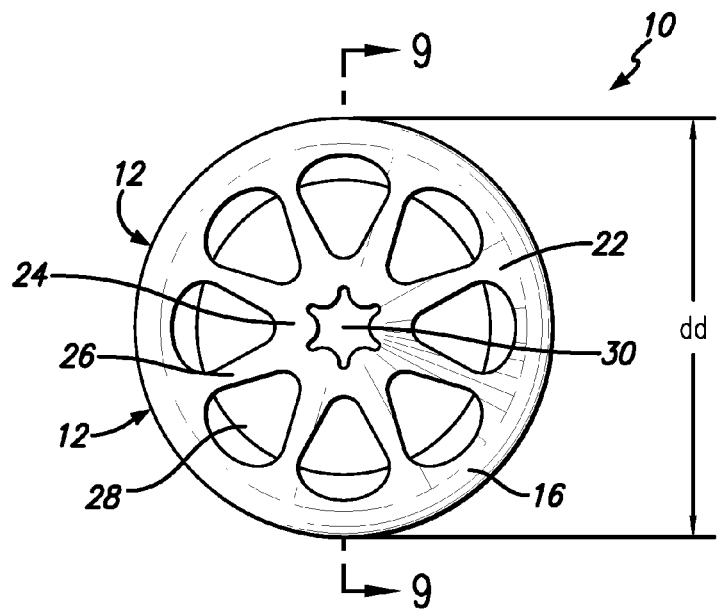
FIG. 4
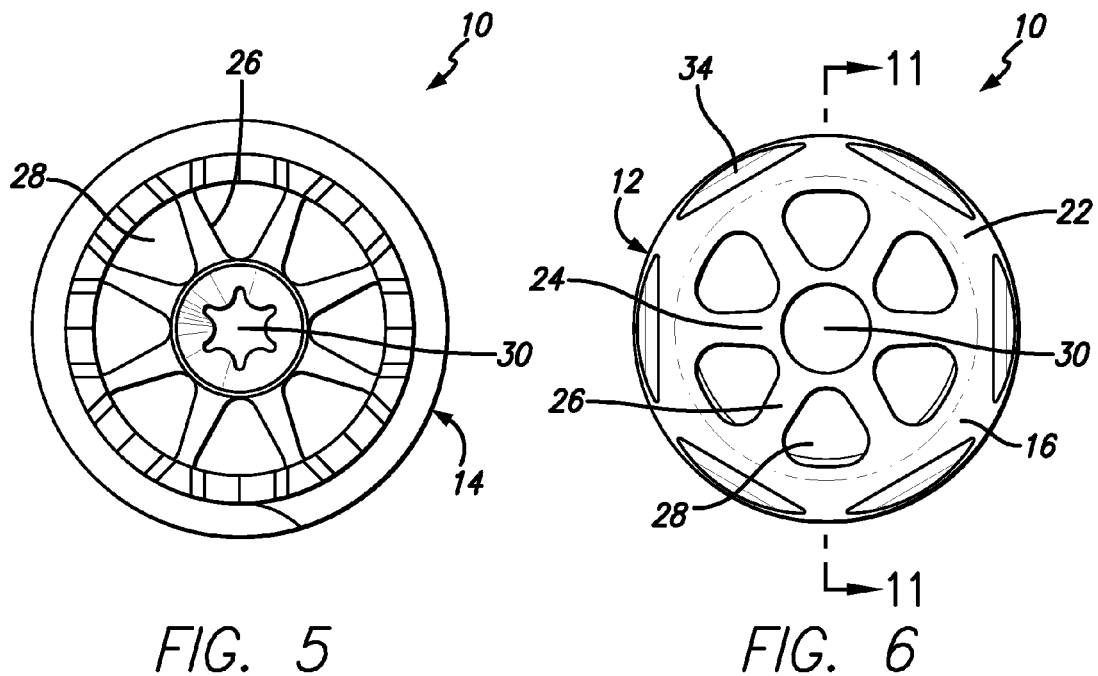
FIG. 5
FIG. 6

METHOD AND DEVICE FOR AMELIORATING JOINT CONDITIONS AND DISEASES

CROSS-REFERENCE TO RELATED APPLICATION

This present Application is a continuation-in-part of U.S. patent application Ser. No. 12/328,493, titled "Joint Support and Subchondral Support System," filed Dec. 4, 2008, the contents of which are incorporated in this disclosure by reference in their entirety.

BACKGROUND

There are a variety of conditions and diseases that impair the integrity and function of human joints. Among these joint conditions and diseases are arthroses, chondromalacia patella, isolated chondral defect, juvenile idiopathic arthritis, ligamentous deficiency arthroses, osteoarthritis (degenerative arthritis or degenerative joint disease), osteonecrosis, osteochondritis dissecans, patellar instability, post-ligamentous injury arthritis, post-meniscectomy arthritis, post-meniscectomy arthroses, post-traumatic arthritis, rheumatoid arthritis and septic arthritis. The incidence of arthritides alone in the United States exceeds 20%, with higher rates among women as compared to men. Treatment of joint conditions and diseases includes surgery and the administration of therapeutic agents. However, none of these treatments ameliorate all of the joint conditions and diseases.

Therefore, there is a need for a new method for ameliorating joint conditions and diseases.

SUMMARY

According to one embodiment of the present invention, there is provided a device for ameliorating joint conditions and diseases. The device comprises a) a first section comprising a joint-ward end, an opposing mating end, and a lateral wall extending between the joint-ward end and the mating end, where the first section further comprises a peripheral column partially forming the lateral wall of the first section, a central column, and three or more than three struts, each strut extending between and connecting the peripheral column and the central column, and each strut thereby supporting the central column, where the joint-ward end further comprises a plurality of fenestrations, where each fenestration is formed by a confluence of the peripheral column, the central column and two adjacent struts of the three or more than three struts, and where the first section further comprises a central aperture within and formed by the central column, and configured to mate with a driver, b) a second section comprising a mating end, an opposing leading end, and a lateral wall extending between the mating end and the leading end, where the lateral wall of the second section comprises threads.

In one embodiment, the device further comprises an axial length, and the axial length is between 5 mm and 30 mm. In another embodiment, the device further comprises an axial length, and the axial length is between 5 mm and 20 mm. In another embodiment, the device further comprises an axial length, and the axial length is between 8 mm and 16 mm. In one embodiment, the first section further comprises a diameter between 5 mm and 30 mm. In another embodiment, the first section further comprises a diameter between 5 mm and 20 mm. In another embodiment, the first section further comprises a diameter between 8 mm and 16 mm. In another embodiment, the first section further comprises an axial length between 1 mm and 2 mm.

In one embodiment, each fenestration comprises a pear or teardrop shape. In another embodiment, one or more than one fenestration comprises a different size, different shape or both a different size and a different shape than one or more than one other fenestration.

In one embodiment, the central aperture comprises a six-pointed star shape. In another embodiment, the central aperture is round and comprises threads. In one embodiment, the peripheral column comprises one or more than one notch.

In one embodiment, the joint-ward end comprises a convex profile as seen on a cross-sectional, lateral perspective view. In another embodiment, the joint-ward end comprises a concave profile as seen on a cross-sectional, lateral perspective view. In another embodiment, the joint-ward end comprises a straight profile as seen on a cross-sectional, lateral perspective view. In one embodiment, the joint-ward end comprises a radius of curvature of between 20 mm and 50 mm. In another embodiment, the joint-ward end comprises a radius of curvature of between 15 mm and 45 mm. In another embodiment, the lateral wall of the first section comprises a generally convex profile as seen on a cross-sectional, lateral perspective view.

In one embodiment, the second section further comprises an axial length between 5 mm and 30 mm. In another embodiment, the second section further comprises an axial length between 5 mm and 20 mm. In another embodiment, the second section further comprises an axial length between 6 mm and 15 mm. In one embodiment, the lateral wall of the second section is generally cylindrical. In another embodiment, the lateral wall of the second section is generally conical, tapering between the mating end and the leading end. In one embodiment, the lateral wall of the second section tapers between 0.2 degrees and 15 degrees. In another embodiment, the lateral wall of the second section tapers between 1 degrees and 5 degrees. In another embodiment, the lateral wall of the second section tapers between 1 degrees and 3 degrees.

In one embodiment, the mating end of the first section and the mating end of the second section mate by a biocompatible adhesive. In another embodiment, the mating end of the first section and the mating end of the second section mate by a mating mechanism that is reversible. In another embodiment, the mating end of the first section and the mating end of the second section mate by a reversible twist locking mechanism. In another embodiment, the first section and the second section are made as a unified whole.

In one embodiment, the leading end comprises a scalloped edge. In another embodiment, the leading end comprises bevels. In another embodiment, the leading end comprises both a scalloped edge and bevels.

In one embodiment, the lateral wall of the second section further comprises a plurality of fenestrations between the threads. In another embodiment, the device further comprises a plurality of fenestrations formed by a confluence of the mating end of the first section and the mating end of the second section. In one embodiment, the device further comprises an insert, where the insert comprises a base and three or more than three extensions connected to the base and arranged radially around the base, and where each of the three or more than three extensions is configured to fit within a corresponding fenestration of the joint-ward end of first section of the device. In one embodiment, the insert further comprises porous biological material impregnated with matrix-promoting substances or serves as a scaffold for progenitor cells, or comprises both porous biological material impregnated with matrix-promoting substances and serves as a scaffold for progenitor cells.

According to another embodiment of the present invention, there is provided a method for ameliorating a joint condition or disease in a patient. The method comprises a) identifying a patient with a joint condition or disease that is suitable for treatment by the method, where the joint comprises a bone with a surface comprising a defect caused by the joint condition or disease, b) accessing the joint, c) placing a guidepin within the center of the defect, d) creating a space in the defect of the bone, e) providing a first device according to the present invention, f) attaching the first device to a driver by mating the distal end of the driver with the central aperture of the first device, and g) screwing the first device into the space using the driver until the joint-ward end of the first device forms a shape that substantially recreates the shape of a normal articulation surface on the bone after implantation.

In one embodiment, the joint is a diarthrodial joint. In another embodiment, the joint is selected from the group consisting of an acetabulofemoral joint, an acromioclavicular joint, a femoropatellar joint, a femorotibial joint, a glenohumeral joint, a humeroradial joint, a humeroulnar joint, an interphalangeal joint, a metacarpal joint, a radioulnar joint and a talocrural joint. In one embodiment, the patient is a human. In one embodiment, the patient is a non-human animal. In one embodiment, the joint condition and disease is selected from the group consisting of arthroses, chondromalacia patella, isolated chondral defect, juvenile idiopathic arthritis, ligamentous deficiency arthroses, osteoarthritis (degenerative arthritis or degenerative joint disease), osteonecrosis, osteochondritis dissecans, patellar instability, post-ligamentous injury arthritis, post-meniscectomy arthritis, post-meniscectomy arthroses, post-traumatic arthritis, rheumatoid arthritis and septic arthritis.

In one embodiment, identifying the patient comprises diagnosing the patient with a joint condition and disease. In another embodiment, diagnosing the patient comprises performing one or more than one of action selected from the group consisting of performing a physical examination, performing a non-invasive imaging examination and performing arthroscopy. In one embodiment, identifying the patient comprises consulting patient records to determine if the patient has a joint condition or disease suitable for treatment by the method. In one embodiment, accessing the joint is accomplished by arthroscopy. In one embodiment, the joint is accomplished by an open surgical procedure.

In one embodiment, the surface of the bone comprises one or more than one abnormality, and the method further comprises using a burr, or a suction shaver, or both a burr and a suction shaver to remove some or all of the one or more than one abnormality thereby creating a smoother articulation surface. In one embodiment, the method further comprises creating one or more than one vascular channel in the bone deep to the space using a drill bit guide positioned over the guidepin and a drill bit passed within the drill bit guide. In another embodiment, the method further comprises injecting a biological material into the first device. In one embodiment, the method further comprises placing an insert in the first device. In one embodiment, the method further comprises placing one or more than one additional device in the defect.

DRAWINGS

These and other features, aspects and advantages of the present invention will become better understood with regard to the following description, appended claims, and accompanying figures where:

FIG. 1 is a lateral perspective view of one embodiment of a device for ameliorating joint conditions and diseases according to the present invention;

FIG. 2 is a top, lateral perspective view of another embodiment of a device for ameliorating joint conditions and diseases according to the present invention;

FIG. 3 is an exploded, top, lateral perspective view of the embodiment of the device for ameliorating joint conditions and diseases shown in FIG. 1;

FIG. 4 is a top perspective view of the embodiment of the device for ameliorating joint conditions and diseases shown in FIG. 1;

FIG. 5 is a bottom perspective view of the embodiment of the device for ameliorating joint conditions and diseases shown in FIG. 1;

FIG. 6 is a top perspective view of the embodiment of the device for ameliorating joint conditions and diseases shown in FIG. 2;

DESCRIPTION

According to one embodiment of the present invention, there is provided a device for ameliorating joint conditions and diseases. According to another embodiment of the present invention, there is provided a method for ameliorating a joint condition or disease in a patient. In one embodiment, the method comprises providing a device according to the present invention. The device and methods will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed and shown are not intended to be limiting nor are they intended to indicate that each step is essential to the method or that each step must occur in the order disclosed but instead are exemplary steps only.

All dimensions specified in this disclosure are by way of example only and are not intended to be limiting, except where the context requires otherwise. Further, the proportions shown in these Figures are not necessarily to scale. As will be understood by those with skill in the art with reference to this disclosure, the actual dimensions and proportions of any device or part of a device disclosed in this disclosure will be determined by its intended use.

Figure 9:
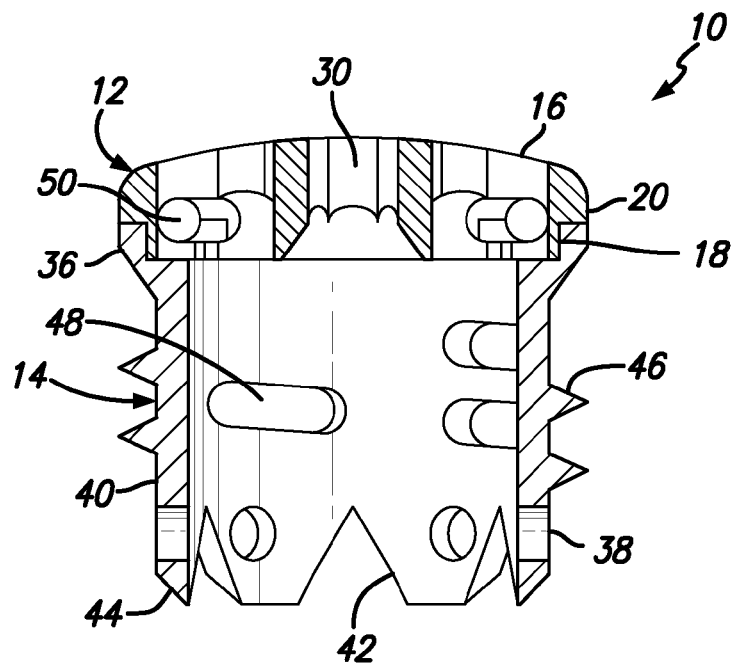
FIG. 9 is a cross-sectional, lateral perspective view of the embodiment of the device for ameliorating joint conditions and diseases shown in FIG. 1 taken along line 9-9.
Figure 10:
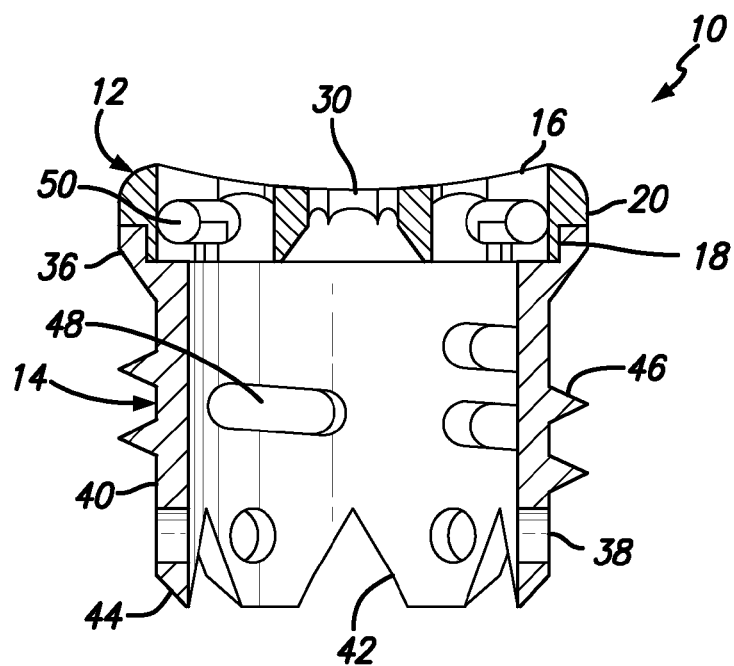
FIG. 10 is a cross-sectional, lateral perspective view of another embodiment of the device for ameliorating joint conditions and diseases according to the present invention.
Figure 11:
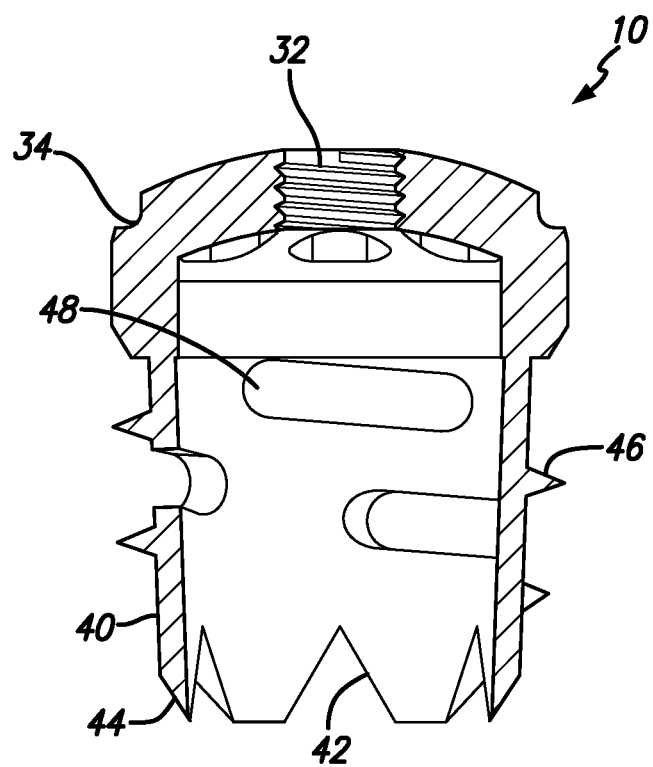
FIG. 11 is a cross-sectional, lateral perspective view of the embodiment of the device for ameliorating joint conditions and diseases shown in FIG. 2 taken along line 11-11.

According to one embodiment of the present invention, there is provided a device for ameliorating joint conditions and diseases. Referring now to FIG. 1 through FIG. 11, there are shown, respectively, a lateral perspective view of one embodiment of a device for ameliorating joint conditions and diseases according to the present invention (FIG. 1); a top, lateral perspective view of another embodiment of a device for ameliorating joint conditions and diseases according to the present invention (FIG. 2); an exploded, top, lateral perspective view of the embodiment of the device for ameliorating joint conditions and diseases shown in FIG. 1 (FIG. 3); a top perspective view of the embodiment of the device for ameliorating joint conditions and diseases shown in FIG. 1 (FIG. 4); a bottom perspective view of the embodiment of the device for ameliorating joint conditions and diseases shown in FIG. 1 (FIG. 5); a top perspective view of the embodiment of the device for ameliorating joint conditions and diseases shown in FIG. 2 (FIG. 6); a top perspective view of another embodiment of the device for ameliorating joint conditions and diseases according to the present invention (FIG. 7); a top perspective view of another embodiment of the device for ameliorating joint conditions and diseases according to the present invention (FIG. 8); a cross-sectional, lateral perspective view of the embodiment of the device for ameliorating joint conditions and diseases shown in FIG. 1 taken along line 9-9 (FIG. 9); a cross-sectional, lateral perspective view of another embodiment of the device for ameliorating joint conditions and diseases according to the present invention (FIG. 10); and a cross-sectional, lateral perspective view of the embodiment of the device for ameliorating joint conditions and diseases shown in FIG. 2 taken along line 11-11 (FIG. 11). As can be seen, the device 10 comprises a first section 12 and a second section 14, and comprises a generally cylindrical shape partially or completely closed at one end. The device 10 further comprises an axial length (a-a). In one embodiment, the axial length (a-a) is between 5 mm and 30 mm. In another embodiment, the axial length (a-a) is between 5 mm and 20 mm. In another embodiment, the axial length (a-a) is between 8 mm and 16 mm. In a preferred embodiment, the axial length (a-a) is 8 mm. In another preferred embodiment, the axial length (a-a) is 12 mm. In another preferred embodiment, the axial length (a-a) is 16 mm.

The first section 12 of the device 10 comprises a joint-ward end 16, an opposing mating end 18, and a lateral wall 20 extending between the joint-ward end 16 and the mating end 18. The first section 12 further comprises a diameter (d-d) and an axial length (b-b). In one embodiment, the diameter (d-d) is between 5 mm and 30 mm. In another embodiment, the diameter (d-d) is between 5 mm and 20 mm. In another embodiment, the diameter (d-d) is between 8 mm and 16 mm. In a preferred embodiment, the diameter (d-d) is 8 mm. In another preferred embodiment, the diameter (d-d) is 12 mm. In another preferred embodiment, the diameter (d-d) is 16 mm. In one embodiment, the axial length (b-b) is between 0.5 mm and 2.5 mm. In another embodiment, the axial length (b-b) is between 1 mm and 2 mm. In a preferred embodiment, the axial length (b-b) is 1.25 mm.

In one embodiment, the first section 12 further comprises a peripheral column 22 partially forming the lateral wall 20, a central column 24, and three or more than three struts 26, each strut 26 extending between and connecting the peripheral column 22 and the central column 24, and each strut 26 thereby supporting the central column 24.

Figure 7:
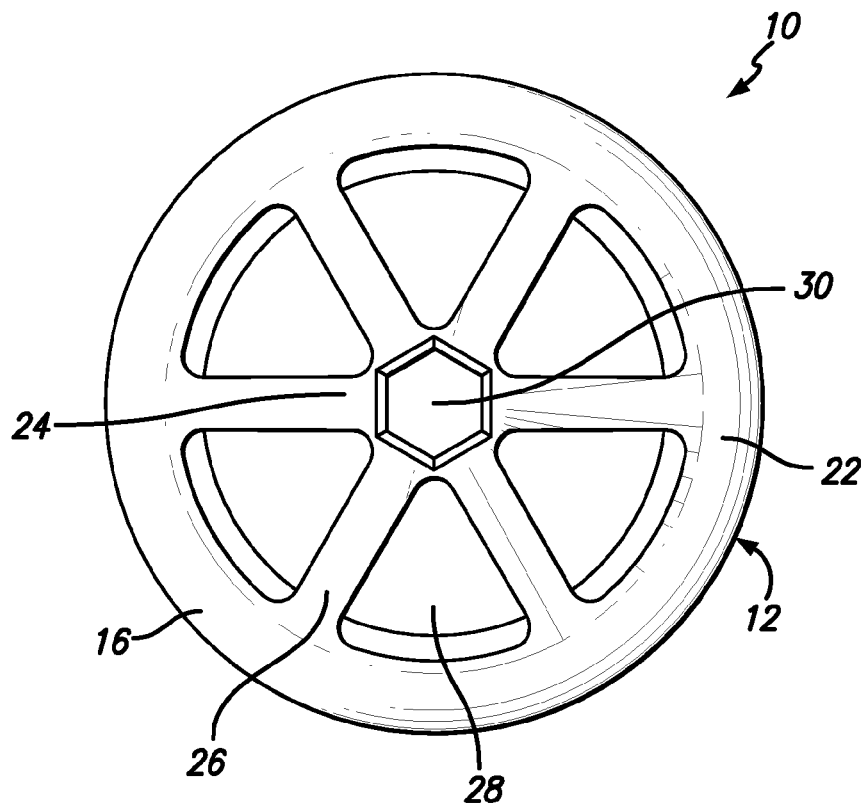
FIG. 7 is a top perspective view of another embodiment of the device for ameliorating joint conditions and diseases according to the present invention.
Figure 8:
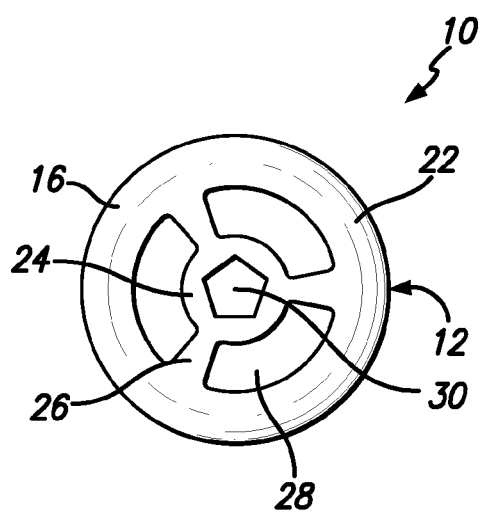
FIG. 8 is a top perspective view of another embodiment of the device for ameliorating joint conditions and diseases according to the present invention.

In one embodiment, the joint-ward end 16 further comprises a plurality of fenestrations 28, where each fenestration 28 is formed by a confluence of the peripheral column 22, the central column 24, and two adjacent struts 26 of the three or more than three struts 26. Each fenestration 28 can comprise any shape suitable for the intended purpose of the device 10, as will be understood by those with skill in the art with respect to this disclosure. In one embodiment, as shown particularly in FIG. 2, FIG. 3, FIG. 4, FIG. 5, FIG. 6 and FIG. 7, each fenestration 28 comprises a pear or teardrop shape. In another embodiment, as shown in FIG. 8, each fenestration 28 comprises a kidney shape. In another embodiment, each fenestration 28 comprises an oval or a round shape. As will be understood by those with skill in the art with respect to this disclosure, all fenestrations 28 on the device 10 can comprise the same size and shape or one or more than one fenestration 28 can comprise a different size, different shape or both a different size and a different shape than one or more than one other fenestration 28. In another embodiment, the joint-ward end 16 can be solid between the central column 24 and the peripheral column 22.

The first section 12 further comprises a central aperture 30 within and formed by the central column 24. The central aperture 30 can extend axially completely through the joint-ward end 16 as shown particularly in FIG. 9, FIG. 10 and FIG. 11, or can be blind-ended extending only partially through within joint-ward end 16. The central aperture 30 is configured to mate with a driver as disclosed below. The central aperture 30 comprises any shape suitable for the intended purpose of the device 10, as will be understood by those with skill in the art with respect to this disclosure. In one embodiment, the central aperture 30 comprises a square shape. In one embodiment, as shown in FIG. 2 and FIG. 6, the central aperture 30 comprises a round shape. In another embodiment, as shown in FIG. 3, FIG. 4 and FIG. 5, the central aperture 30 comprises a six-pointed star shape. In another embodiment, as shown in FIG. 7, the central aperture 30 comprises a pentagonal shape. In another embodiment, as shown in FIG. 8, the central aperture 30 comprises a hexagonal shape. In one embodiment, as shown in FIG. 2 and FIG. 11, the central aperture 30 comprises threads 32 to assist in mating with a driver.

In one embodiment, peripheral column 22 of the first section 12 comprises one or more than one notch 34 as seen in FIG. 2, FIG. 6 and FIG. 11. The one or more than one notch can be used to mate with a driver in addition to the central aperture 30 or instead of the central aperture 30, as will be understood by those with skill in the art with respect to this disclosure.

The joint-ward end 16 of the first section 12 of the device 10 performs a partial load-bearing function after implantation, and comprises a shape suitable to substantially match the shape of the articulation surface that the device 10 recreates on the bone after implantation, as will be understood by those with skill in the art with respect to this disclosure. Therefore, the joint-ward end 16 can have either a convex profile as seen on a cross-sectional, lateral perspective view, as shown in FIG. 9 and FIG. 11, a concave profile as seen on a cross-sectional, lateral perspective view, as shown in FIG. 10, or a straight profile as seen on a cross-sectional, lateral perspective view. In one embodiment, the joint-ward end has a convex profile having a radius of curvature of between 10 mm and 50 mm. In another embodiment, the joint-ward end has a convex profile as seen on a cross-sectional, lateral perspective view with a radius of curvature of between 15 mm and 45 mm. In another embodiment, the joint-ward end has a convex profile as seen on a cross-sectional, lateral perspective view with a radius of curvature of between 20 mm and 30 mm. In one embodiment, the joint-ward end has a concave profile as seen on cross-sectional, lateral perspective view with a radius of curvature of between 10 mm and 50 mm. In another embodiment, the joint-ward end has a concave profile as seen on cross-sectional, lateral perspective view with a radius of curvature of between 15 mm and 45 mm. In another embodiment, the joint-ward end has a concave profile as seen on cross-sectional, lateral perspective view with a radius of curvature of between 20 mm and 30 mm. In a preferred embodiment, the joint-ward end 16 comprises a smooth surface facing the center of joint after implantation, as will be understood by those with skill in the art with respect to this disclosure. In a preferred embodiment, the joint-ward end 16 is polished to make the surface smooth.

The lateral wall 20 of the first section 12 can be any shape suitable for the intended purpose of the device 10, as will be understood by those with skill in the art with respect to this disclosure. In a preferred embodiment, the lateral wall 20 of the first section 12 comprises a generally convex profile as seen on a cross-sectional, lateral perspective view, as shown in FIG. 9 and FIG. 11. This convex profile advantageously provides a smooth transition to and encourages biologic bonding to surrounding cartilage and bone after implantation, as will be understood by those with skill in the art with respect to this disclosure.

The device 10 further comprises a second section 14. The second section 14 of the device 10 comprises a mating end 36, an opposing leading end 38, and a lateral wall 40 extending between the mating end 36 and the leading end 38. The second section 14 further comprises an axial length (c-c). In one embodiment, the axial length (c-c) is between 5 mm and 30 mm. In another embodiment, the axial length (c-c) is between 5 mm and 20 mm. In another embodiment, the axial length (c-c) is between 6 mm and 15 mm. In a preferred embodiment, the axial length (c-c) is 6 mm. In another preferred embodiment, the axial length (c-c) is 10 mm. In another preferred embodiment, the axial length (c-c) is 15 mm. In one embodiment, the lateral wall 40 of the second section 14 is generally cylindrical as seen in FIG. 1, FIG. 9 and FIG. 10. In another embodiment, the lateral wall 40 of the second section 14 is generally conical, tapering between the mating end 36 and the leading end 38 as seen in FIG. 11. In one embodiment, the lateral wall 40 of the second section 14 tapers between 0.2 degrees and 15 degrees. In another embodiment, the lateral wall 16 tapers between 1 degrees and 5 degrees. In another embodiment, the lateral wall 40 of the second section 14 tapers between 1 degrees and 3 degrees.

The mating end 36 of the second section 14 of the device 10 is configured to mate with the mating end 18 of the first section 12 of the device 10. The mating end 18 of the first section 12 and the mating end 36 of the second section 14 can comprise any mating mechanism suitable for the intended purpose of the device 10 can be used, as will be understood by those with skill in the art with respect to this disclosure. In one embodiment, the mating end 18 of the first section 12 and the mating end 36 of the second section 14 mate by a suitable biocompatible adhesive, as will be understood by those with skill in the art with respect to this disclosure. In a preferred embodiment, the mating mechanism is reversible, allowing an interchange of an alternate first section 12 to a specific second section 14 so that the device 10 can be reconfigured as needed for contouring to a particular joint surface, thereby decreasing the number of second sections 14 that need to be stored on site, as will be understood by those with skill in the art with respect to this disclosure. In one embodiment, the mating end 18 of the first section 12 and the mating end 36 of the second section 14 mate by a reversible twist locking mechanism, as will be understood by those with skill in the art with respect to this disclosure. In another embodiment, the first section 12 and the second section 14 are made as a unified whole as shown in FIG. 11 and are not separable.

The leading end 38 of the second section 14 of the device 10 is configured to place the device 10 into a prepared space made according to a method according to the present invention. In one embodiment, the leading end 38 comprises a scalloped edge 42. In another embodiment, the leading end 38 comprises bevels 44. In a preferred embodiment, the leading end 38 comprises both a scalloped edge 42 and bevels 44 as shown particularly in FIG. 1, FIG. 3, FIG. 5 and FIG. 6.

The lateral wall 40 of the second section 14 of the device 10 extends between the mating end 36 and the leading end 38. The lateral wall 40 of the second section 14 comprises threads 46 for anchoring the device 10 within the bone. In one embodiment, the lateral wall 40 of the second section 14 further comprises a plurality of fenestrations 48 between the threads 46. In a preferred embodiment, the device 10 further comprises a plurality of fenestrations 50 formed by a confluence of the mating end 18 of the first section 12 and the mating end 36 of the second section 14. Each fenestration 48, 50 can comprise any shape suitable for the intended purpose of the device 10, as will be understood by those with skill in the art with respect to this disclosure. In a preferred embodiment, each fenestration 48, 50 is oval or round. In one embodiment, the lateral wall 40 of the second section 14 is textured to promote bony ingrowth after implantation, as will be understood by those with skill in the art with respect to this disclosure.

The first section 12 and the second section 14 can comprise any material suitable for the intended purpose of the device 10, as will be understood by those with skill in the art with respect to this disclosure. In one embodiment, the first section 12 comprises a material selected from the group consisting of a biocompatible plastic, a biocomposite polymer, a metal and a metal alloy. In one embodiment, the first section 12 comprises a material selected from the group consisting of carbon fiber, cobalt chrome, nitinol, polycaprolactone (PCL), polyether-ether-ketone (PEEK), tantalum and titanium. In one embodiment, the second section 14 comprises a material selected from the group consisting of a biocompatible plastic, a biocomposite polymer, a metal and a metal alloy. In one embodiment, the second section 14 comprises a material selected from the group consisting of carbon fiber, cobalt chrome, nitinol, polycaprolactone (PCL), polyether-ether-ketone (PEEK), tantalum and titanium. In one embodiment, the first section 12 comprises a first material and the second section 14 comprises a second material, where the first material and the second material are the same material. In another embodiment, the first section 12 comprises a first material and the second section 14 comprises a second material, where the first material and the second material are the different materials.

Figure 12:
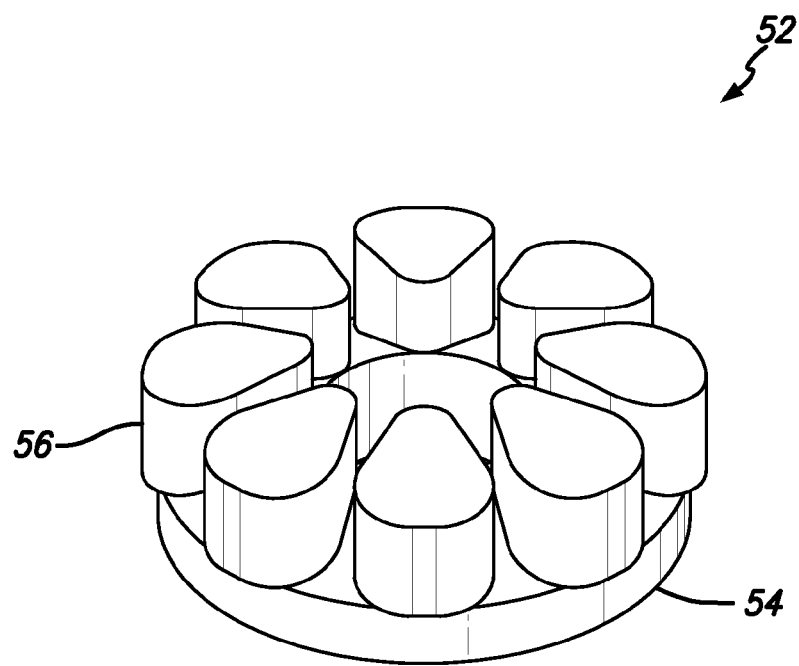
FIG. 12 is a top, lateral perspective view of one embodiment of an insert according to the present invention for use with a device for ameliorating joint conditions and diseases according to the present invention.
Figure 13:
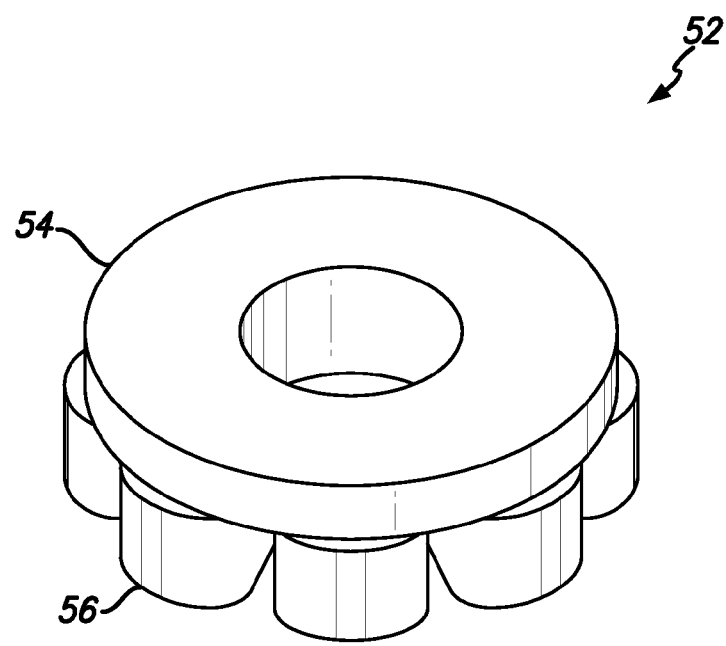
FIG. 13 is a bottom, lateral perspective view of the embodiment of the insert shown in FIG. 12.
Figure 14:
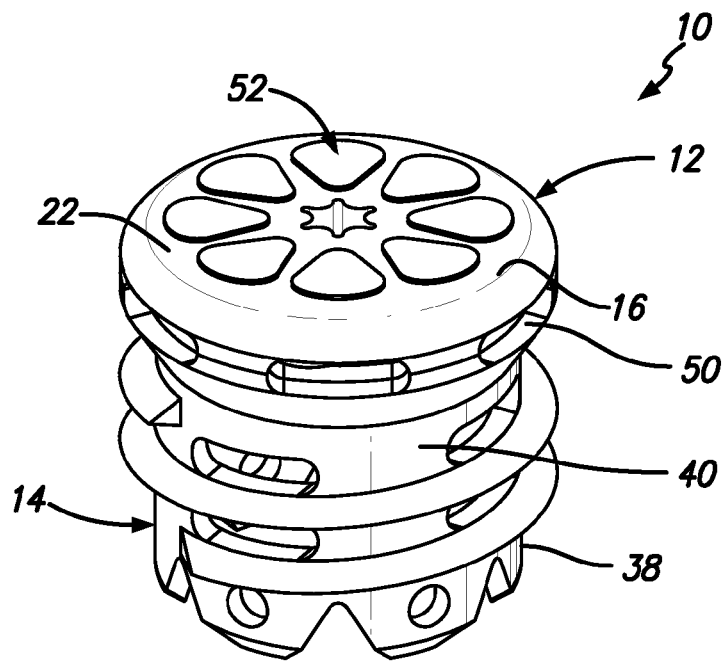
FIG. 14 is a top, lateral perspective view of one embodiment of the device for ameliorating joint conditions and diseases shown in FIG. 1 with the insert shown in FIG. 12 according to the present invention affixed to the device.

In one embodiment, the device 10 further comprises an insert 52. Referring now to FIG. 12, FIG. 13, FIG. 14 and FIG.

Figure 15:
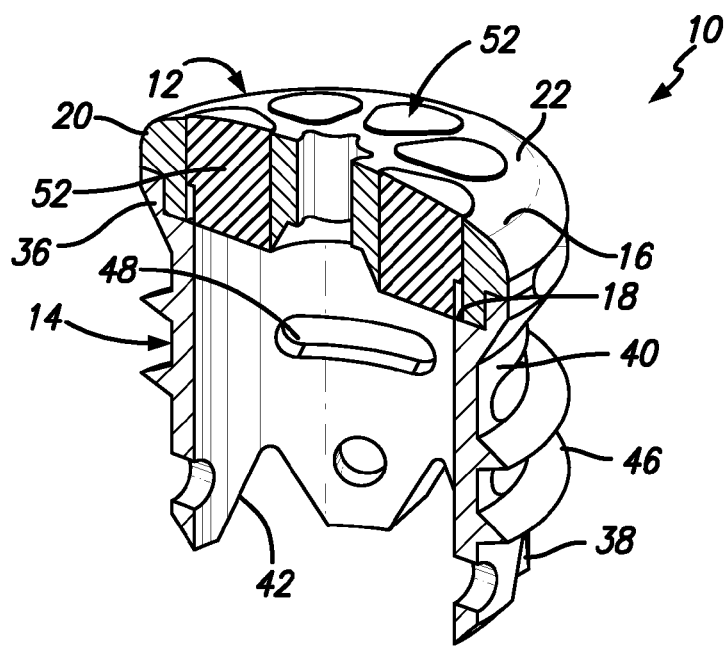
FIG. 15 is a cross-sectional view of the device for ameliorating joint conditions and diseases shown in FIG. 1 with the insert shown in FIG. 12 according to the present invention affixed to the device.
Figure 16:
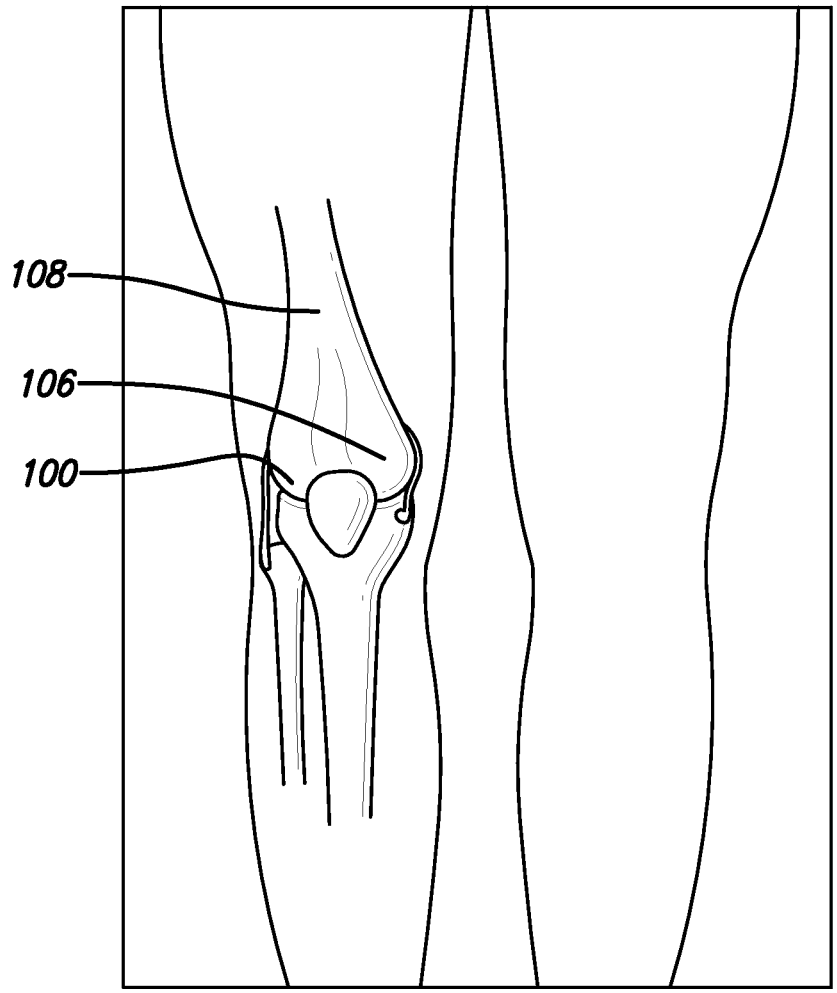
FIG. 16 through FIG. 35 are schematic depictions of some steps of a method for ameliorating joint conditions and diseases according to the present invention.

15, there are shown, respectively, a top, lateral perspective view of one embodiment of an insert according to the present invention for use with a device for ameliorating joint conditions and diseases according to the present invention (FIG. 12); a bottom, lateral perspective view of the embodiment of the insert shown in FIG. 12 (FIG. 13); a top, lateral perspective view of one embodiment of the device for ameliorating joint conditions and diseases shown in FIG. 1 with the insert shown in FIG. 12 according to the present invention affixed to the device (FIG. 14); and a cross-sectional view of the device for ameliorating joint conditions and diseases shown in FIG. 1 with the insert shown in FIG. 12 (FIG. 15). As can be seen, the insert 52 comprises a base 54 and three or more than three extensions 56 connected to the base 54 and arranged radially around the base 54. Each of the three or more than three extensions 56 is configured to fit within a corresponding fenestration 28 of the joint-ward end 16 of the first section 12 of the device 10, such that when the insert 52 is mated to the first section 12 of the device 10, the insert 52 occupies each of the three or more than three fenestrations 28 as shown particularly in FIG. 5. The insert 52 comprises porous biological material impregnated with matrix-promoting substances or serves as a scaffold for progenitor cells, or comprises both porous biological material impregnated with matrix-promoting substances and serves as a scaffold for progenitor cells.

The device 10 can be made by any suitable method, as will be understood by those with skill in the art with respect to this disclosure. In one embodiment, the first section 12 and the second section 14 are machined from modular parts such as by direct metal laser sintering, as will be understood by those with skill in the art with respect to this disclosure.

According to another embodiment of the present invention, there is provided a method for ameliorating a joint condition or disease in a patient. Referring now to FIG. 16 through FIG. 35, there are shown schematic depictions of some steps of a method for ameliorating joint conditions and diseases according to the present invention. The Figures show the embodiment of the method being used on a femorotibial joint 100 to ameliorate an arthritic condition which has caused a defect 102 on an articulation surface 104 of a bone or joint, shown here as on the medial condyle 106 of the femur 108.

The method comprises identifying a patient with a joint condition or disease that is suitable for treatment by the present method, where the joint comprises a bone with a surface comprising a defect caused by the joint condition or disease. As will be understood by those with skill in the art with respect to this disclosure, the joint can be any joint with a hyaline cartilage bearing surface, joint capsule, and synovial fluid. In one embodiment, the joint is a diarthrodial joint (also know as a synovial joint). In one embodiment, the joint is selected from the group consisting of an acetabulofemoral joint, an acromioclavicular joint, a femoropatellar joint, a femorotibial joint, a glenohumeral joint, a humeroradial joint, a humeroulnar joint, an interphalangeal joint, a metacarpal joint, a radioulnar joint and a talocrural joint. In one embodiment, the patient is a human. In one embodiment, the patient is a non-human animal. In a preferred embodiment, the joint condition and disease is selected from the group consisting of arthroses, chondromalacia patella, isolated chondral defect, juvenile idiopathic arthritis, ligamentous deficiency arthroses, osteoarthritis (degenerative arthritis or degenerative joint disease), osteonecrosis, osteochondritis dissecans, patellar instability, post-ligamentous injury arthritis, post-meniscectomy arthritis, post-meniscectomy arthroses, post-traumatic arthritis, rheumatoid arthritis and septic arthritis. In one embodiment, identifying the patient comprises diagnosing the patient with a joint condition and disease. In one embodiment, diagnosing the patient comprises performing one or more than one of action selected from the group consisting of performing a physical examination, performing a non-invasive imaging examination (such as magnetic resonance imaging, computerized tomography and ultrasound) and performing arthroscopy. In another embodiment, identifying the patient comprises consulting patient records to determine if the patient has a joint condition or disease suitable for treatment by the present method.

Next, the method further comprises accessing the joint 100. In one embodiment, accessing the joint 100 is accomplished by arthroscopy. In another embodiment, accessing the joint 100 is accomplished by an open surgical procedure, such as for example a mini-open procedure.

Figure 17:
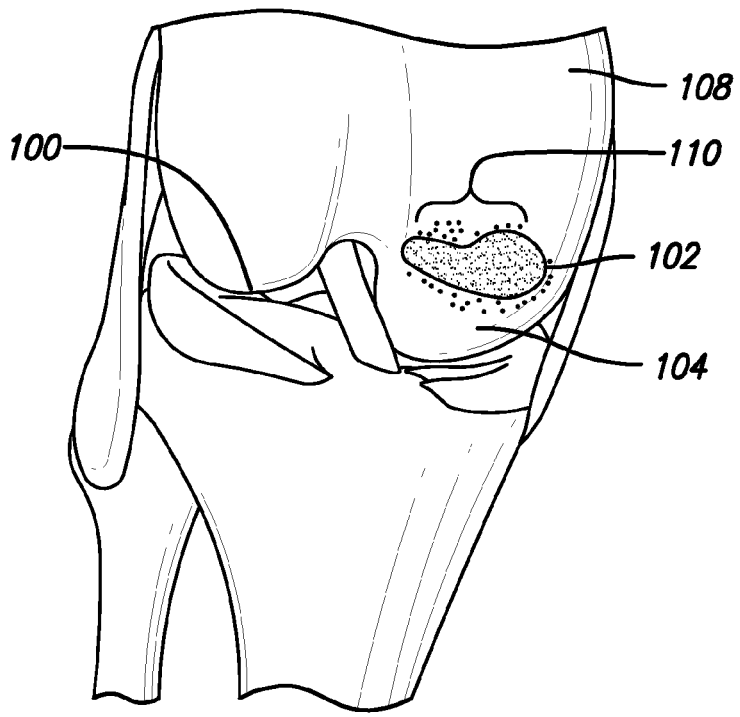
Figure 18:
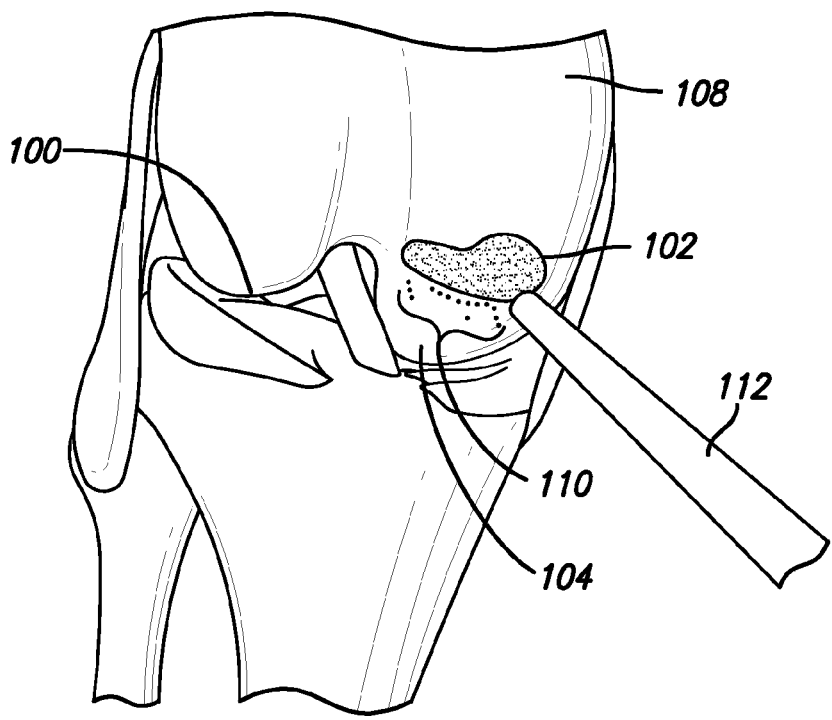
Figure 19:
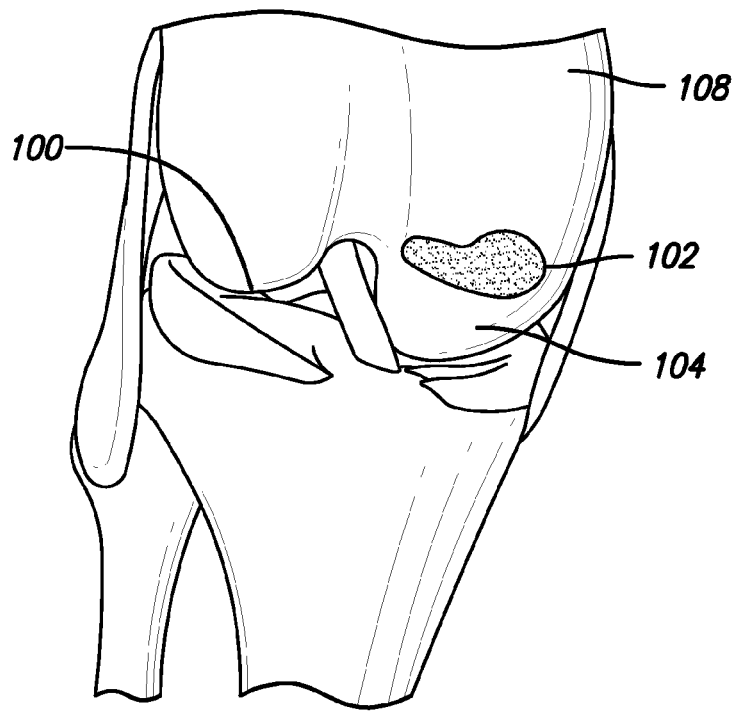

In one embodiment, as shown in FIG. 17 and FIG. 18, the surface 104 of the bone comprises an abnormality 110 (such as for example area cartilage softening, thinning, damage, or absence), and the method further comprises using a burr, or a suction shaver, or both a burr and a suction shaver 112 to remove some or all of the abnormalities 110 thereby creating a smoother articulation surface 104 as shown in FIG. 19.

Figure 20:
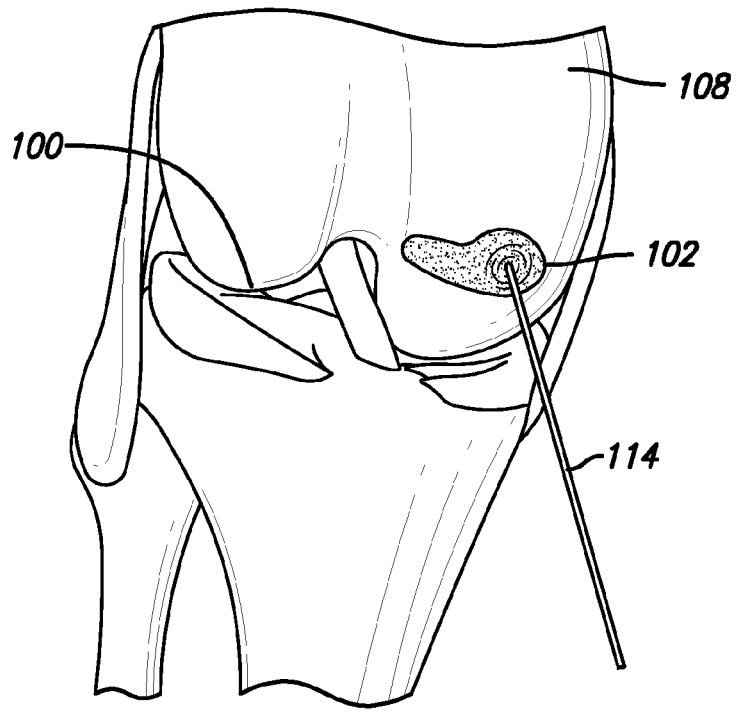

Then, the method further comprises placing a guidepin 114 within the center of the defect 102 as shown in FIG. 20.

Figure 21:
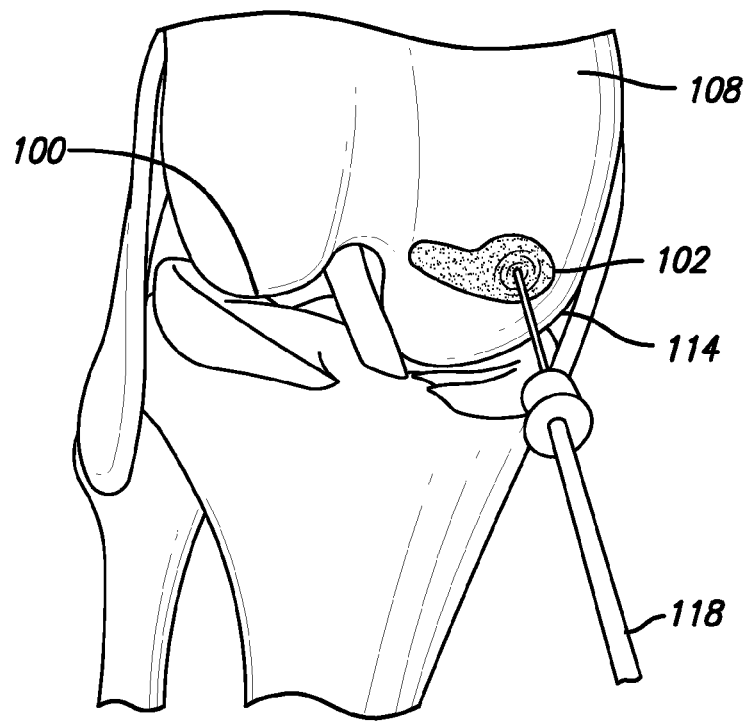
Figure 22:
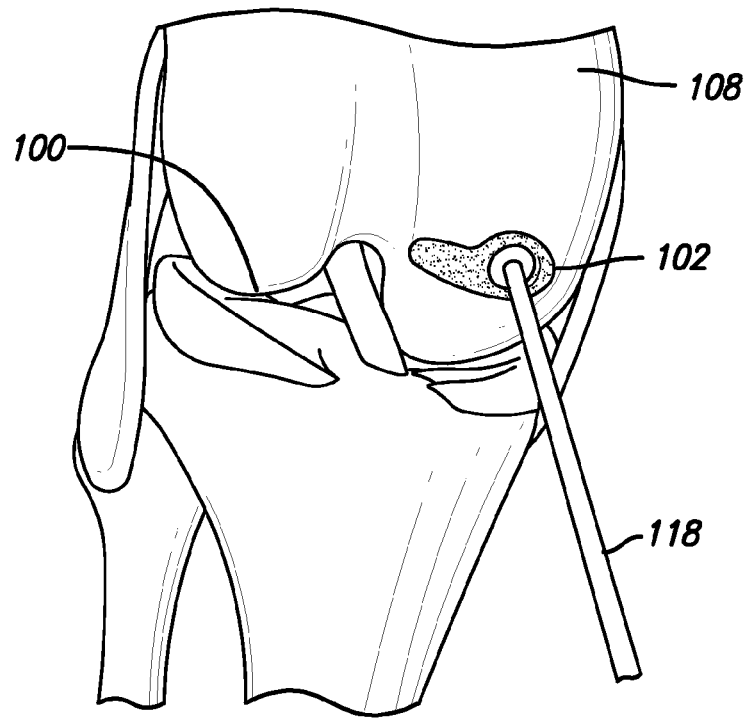
Figure 23:
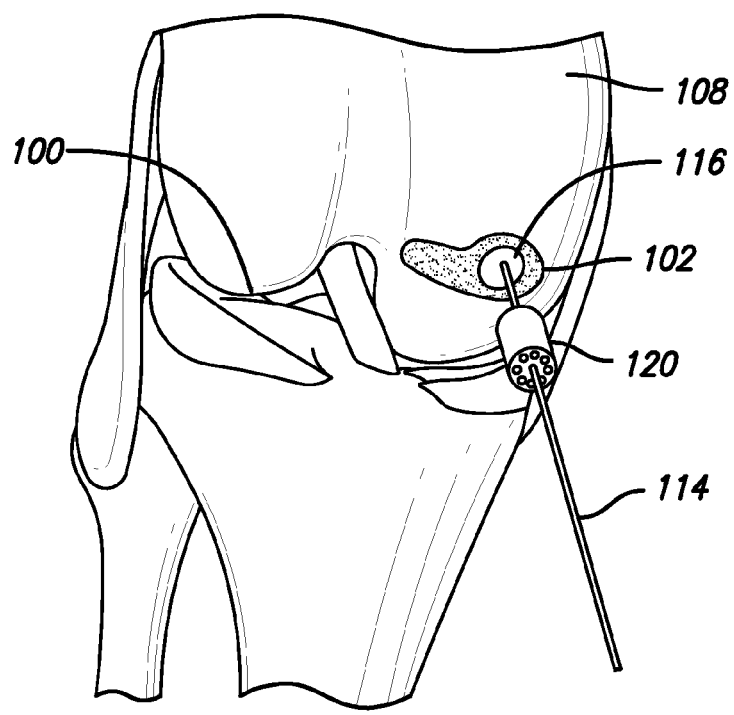

Next, the method further comprises creating a space 116 in the defect 102 of the bone for a device. In one embodiment, the space 116 is created using a bone reamer 118 placed over the guidepin 114 to core and plane the surface of the defect 102 as shown in FIG. 21, FIG. 22 and FIG. 23. The bone reamer 118 is then removed leaving the guidepin 114 in place.

Figure 24:
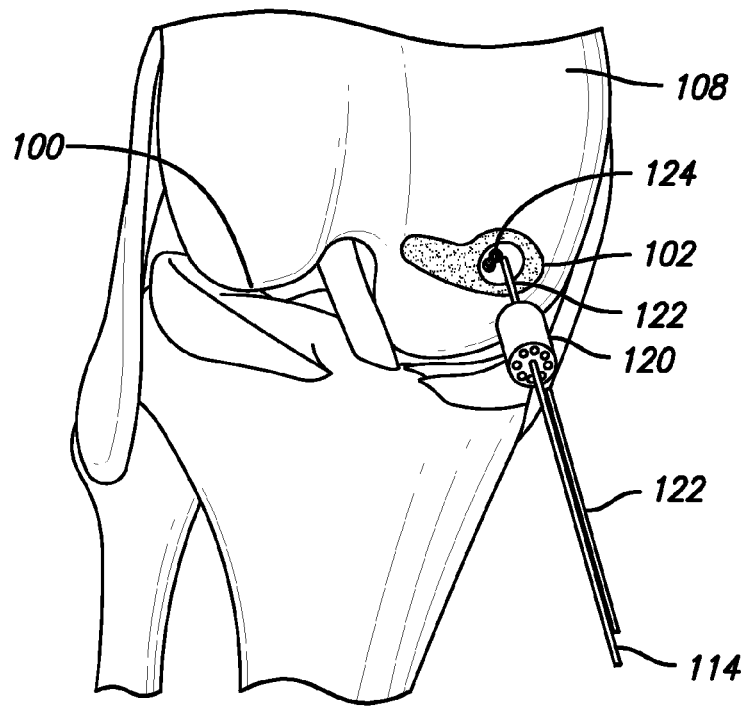
Figure 25:
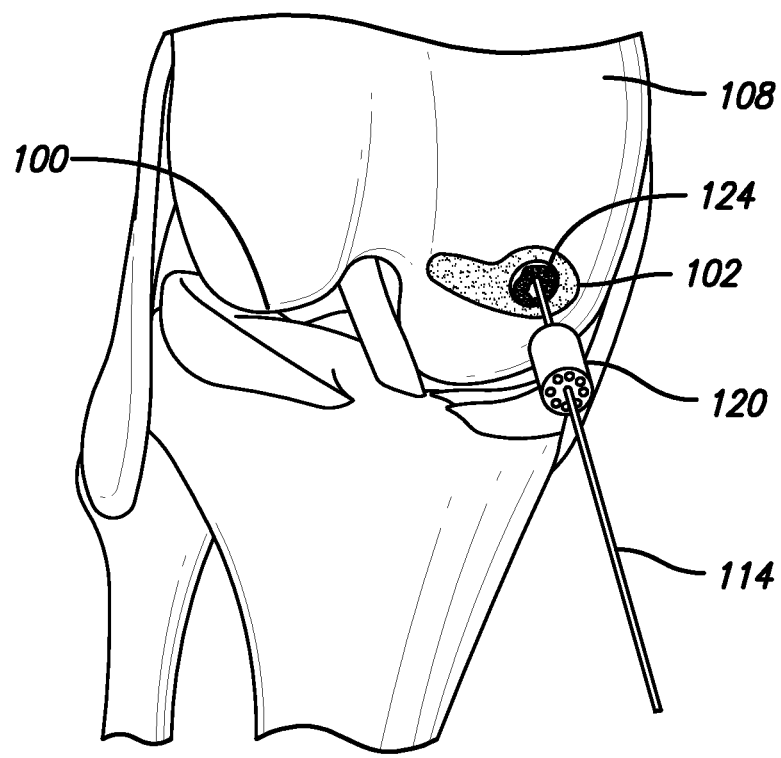

In one embodiment, the method further comprises creating one or more than one vascular channel in the bone deep to the space 116 using a drill bit guide 120 positioned over the guidepin 114 and a drill bit 122 passed within the drill bit guide 120 as shown in FIG. 23, FIG. 24 and FIG. 25. Confirmation of creation of the one or more than one vascular channel is made by the presence of blood 124 leaking into the space 116 from the one or more than one vascular channel. The drill bit guide 120 and drill bit 122 are then removed leaving the guidepin 114 in place.

Figure 26:
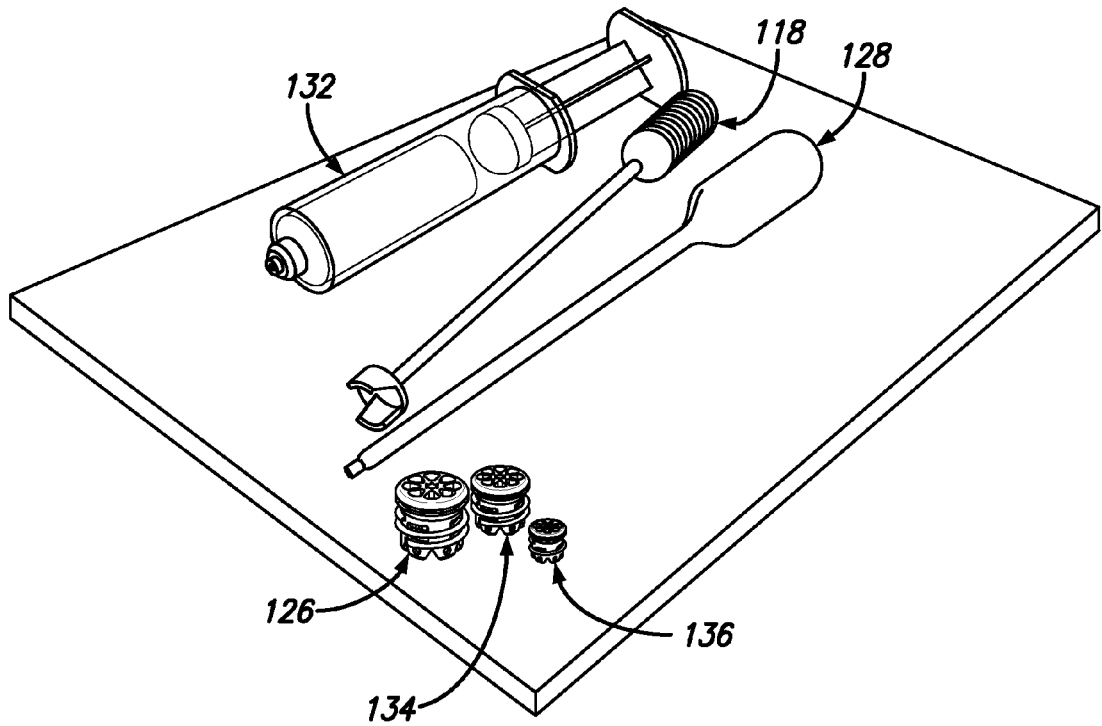
Figure 27:
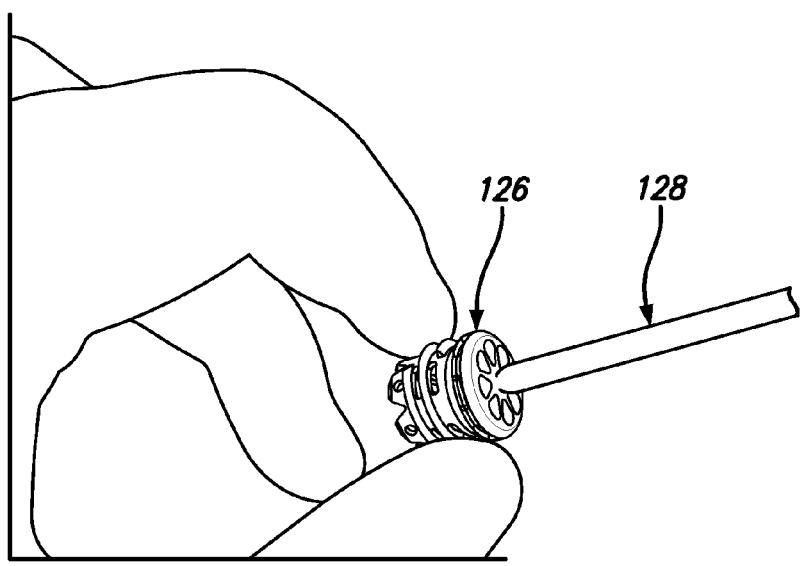

Next, the method further comprises providing a first device 126 for ameliorating joint conditions and diseases suitable for ameliorating the joint condition or disease of the patient as can be seen in FIG. 26. In one embodiment, the first device 126 is a device according to the present invention. The first device 126 provided has a size suitable for incorporation into the space 116 made in the defect 102, and the joint-ward end of the first device 126 comprises a shape suitable to substantially match the shape of the articulation surface 104 that the first device 126 recreates on the bone after implantation, as will be understood by those with skill in the art with respect to this disclosure. Referring now to FIG. 27, the first device 126 is attached to a driver 128, such as for example by mating the distal end of the driver 128 with the central aperture of the first device 126.

Figure 28:
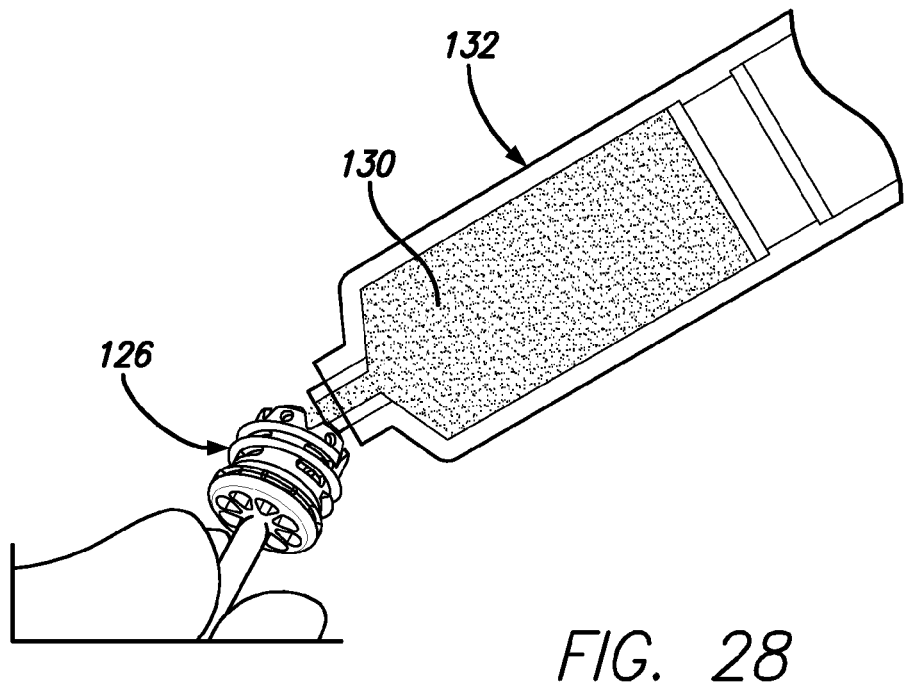
Figure 29:
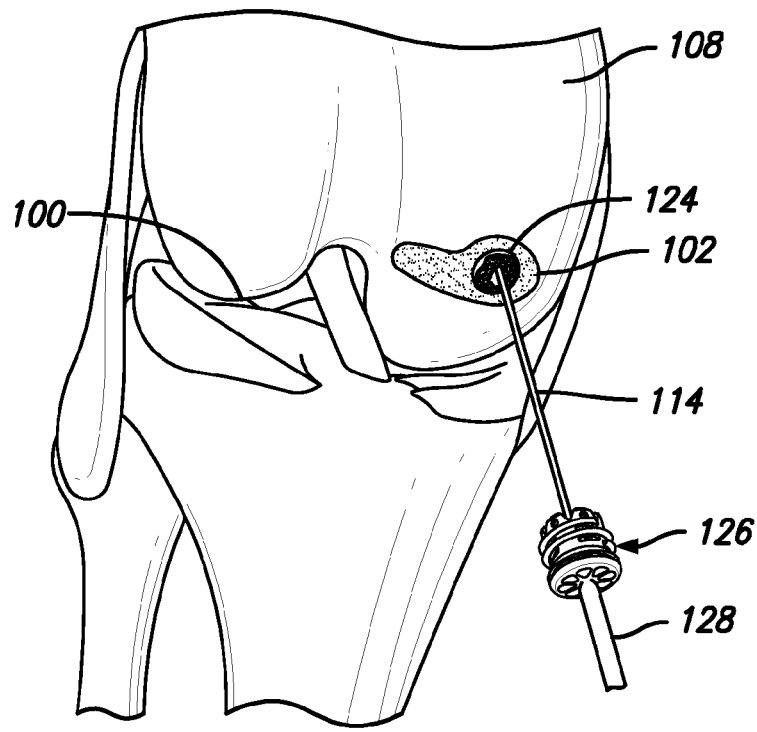
Figure 30:
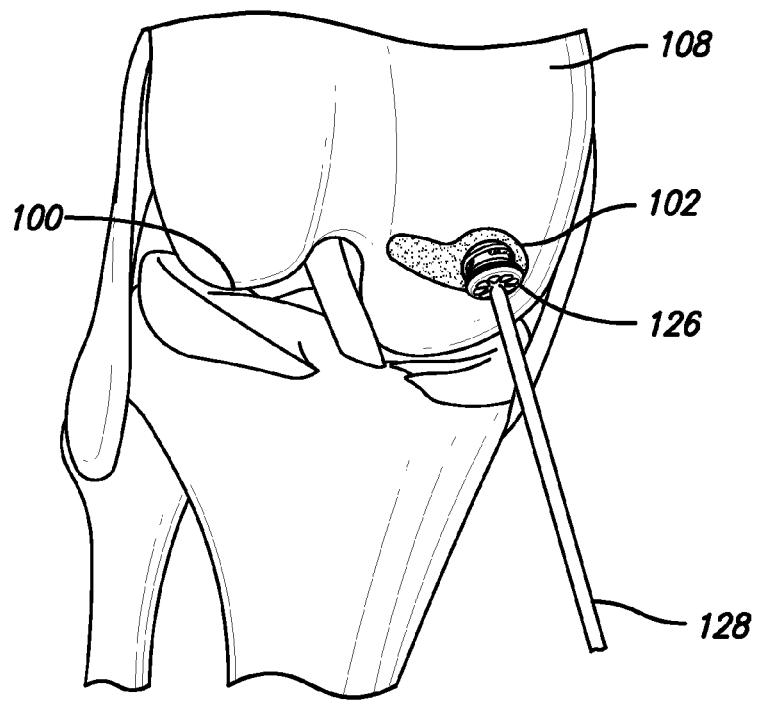
Figure 31:
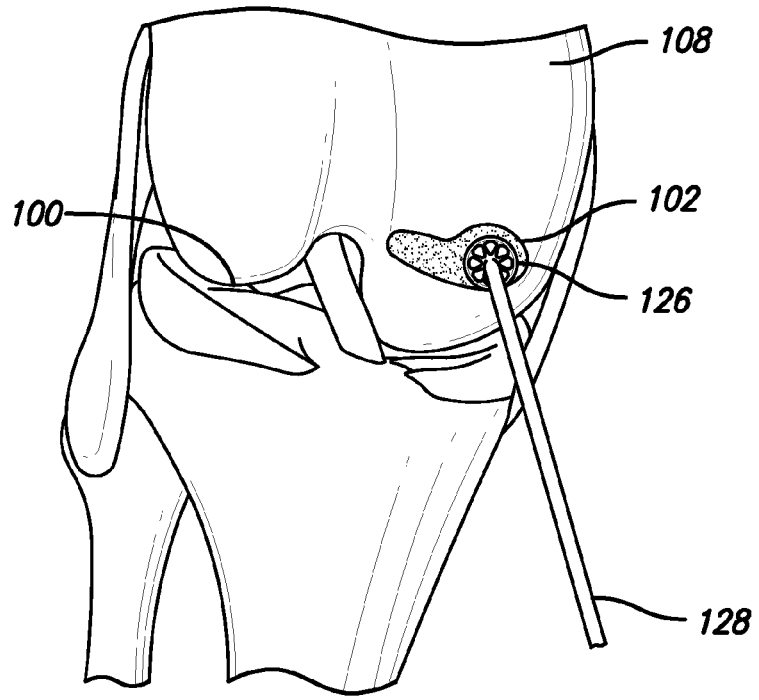
Figure 32:
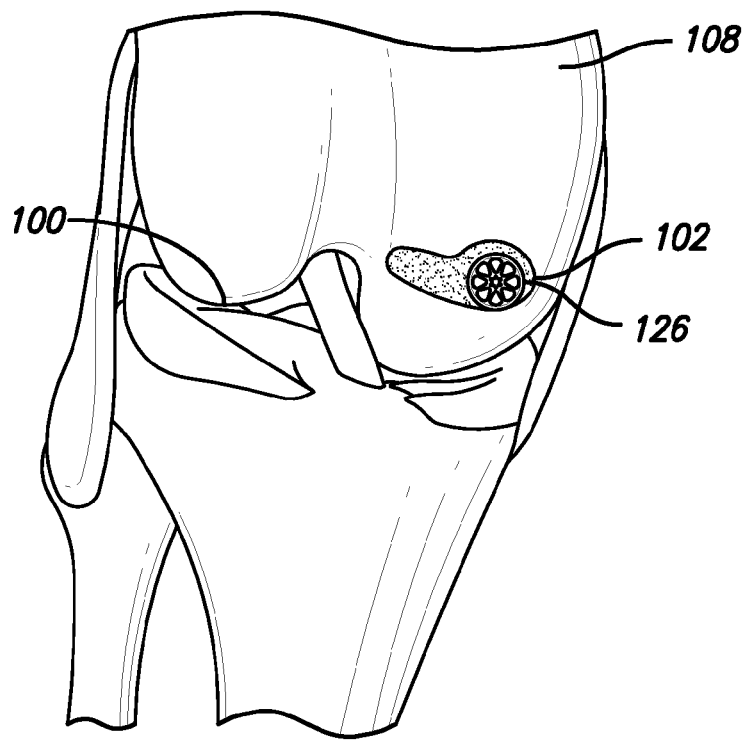

In one embodiment, the method further comprises injecting a biologic material, such as for example stem cells or platelet rich plasma, or both stem cells and platelet rich plasma 130 into the first device 126 using an injector 132 as shown in FIG. 28. In one embodiment, the method further comprises placing an insert according to the present invention in the first device 126 instead of injecting a biocompatible bone cement in the first device 126. In one embodiment, the insert is a biological material according to the present invention.

Figure 33:
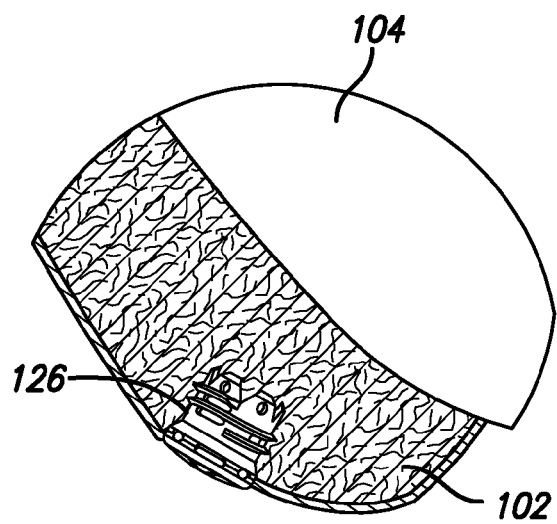

Then, the method further comprises screwing the first device 126 into the space 116 using the driver 128, as shown in FIG. 29, FIG. 30, FIG. 31 and FIG. 32. FIG. 33 is a partial, lateral cross-section of the medial condyle 106 at the site of the defect 102 showing placement of the first device 126. As can be seen, the joint-ward end of the first device 126 forms a shape that substantially recreates the shape of a normal articulation surface on the bone after implantation.

Figure 34:
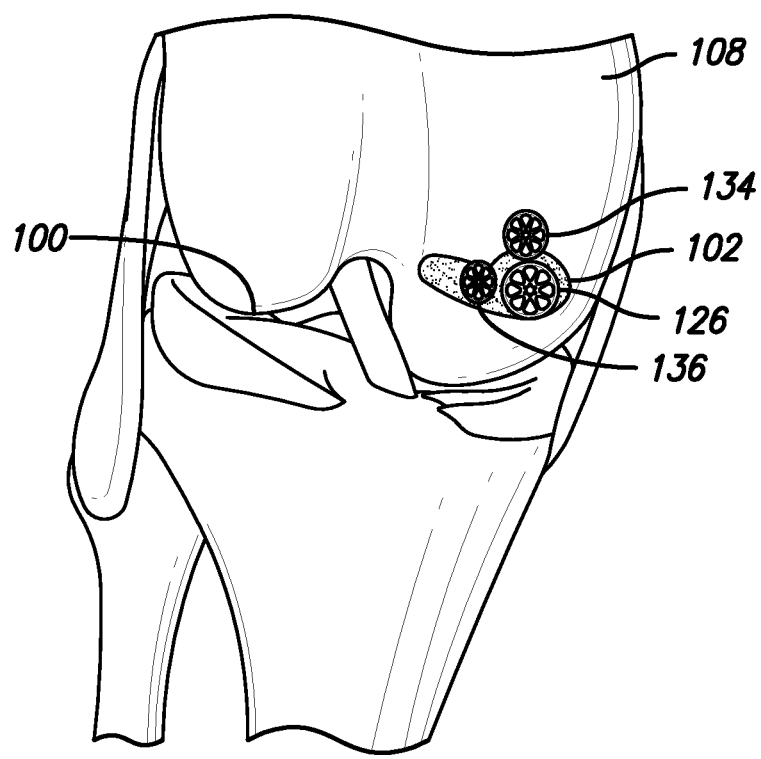

In one embodiment, as can be seen in FIG. 26 and FIG. 34, the method further comprises placing one or more than one additional device 134, 136 in the defect 102. In one embodiment, the one or more than one additional device is one additional device. In another embodiment, one or more than one additional device is two additional devices. As will be understood by those with skill in the art with respect to this disclosure, the one or more than one additional device 134, 136 can be the same as the first device in terms of size and shape or can be different than the first device in terms of size and shape.

Figure 35:
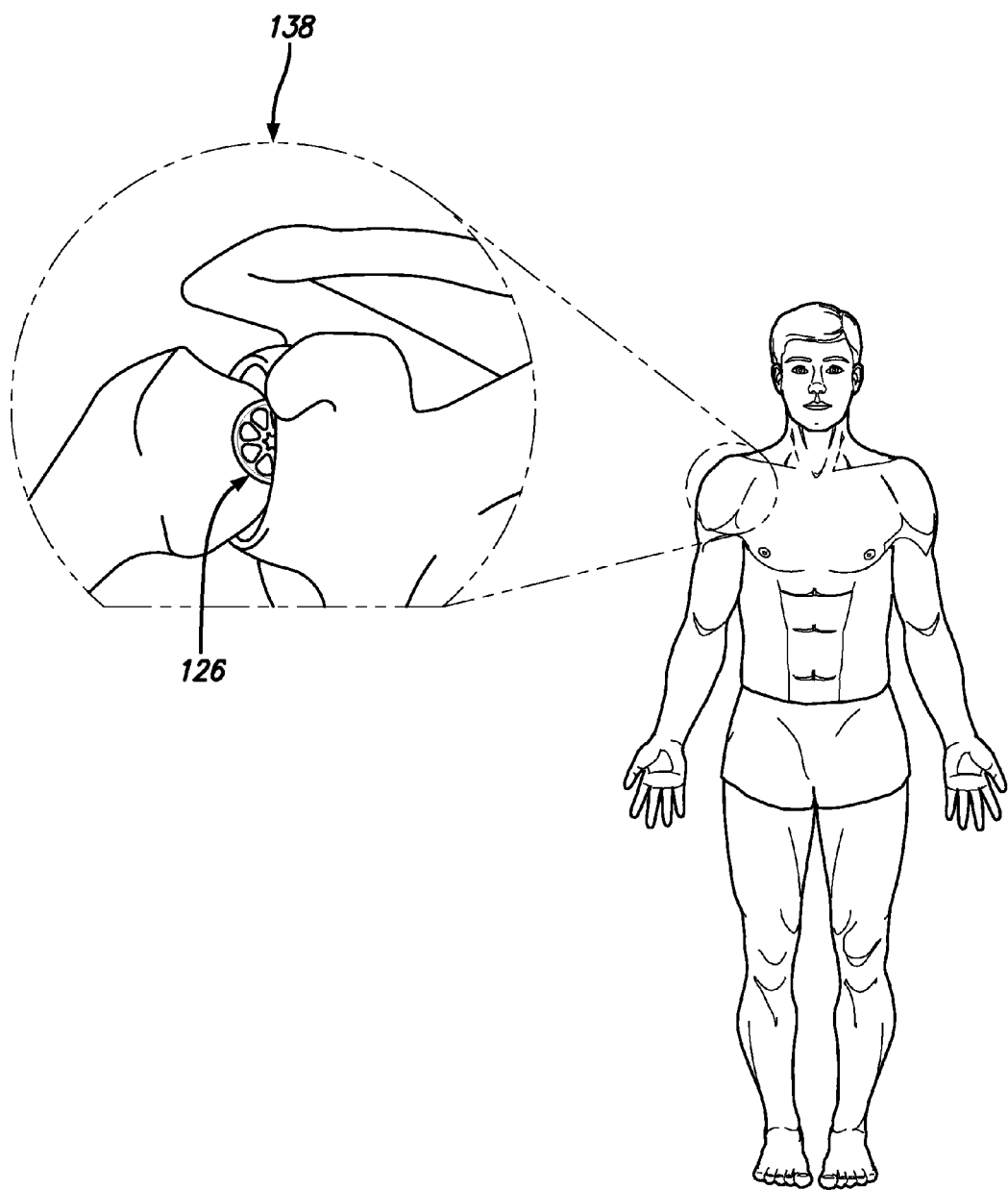

Though the method of the present invention has been disclosed with respect to a defect 102 in a femorotibial joint 100, corresponding methods can be used with other joints. FIG. 35 is a partial, lateral cross-section of a glenohumeral joint 138 at the site of a defect showing placement of a device for ameliorating joint conditions and diseases according to the present invention.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A method for ameliorating a joint condition or disease in a patient, the method comprising:
    a) identifying a patient with a joint condition or disease that is suitable for treatment by the method, where the joint comprises a bone with a surface comprising a defect caused by the joint condition or disease;
    b) accessing the joint;
    c) placing a guidepin within the center of the defect;
    d) creating a space in the defect of the bone;
    e) providing a first device for ameliorating joint conditions and diseases, the first device comprising:
    i) a first section comprising a joint-ward end, an opposing mating end, and a lateral wall extending between the joint-ward end and the mating end;
    where the first section further comprises a peripheral column partially forming the lateral wall of the first section, a central column, and three or more than three struts, each strut extending between and connecting the peripheral column and the central column, and each strut thereby supporting the central column;
    where the joint-ward end further comprises a plurality of fenestrations, where each fenestration is formed by a confluence of the peripheral column, the central column and two adjacent struts of the three or more than three struts; and
    where the first section further comprises a central aperture within and formed by the central column, and configured to mate with an introducer; and
    ii) a second section comprising a mating end, an opposing leading end, and a lateral wall extending between the mating end and the leading end;
    where the lateral wall of the second section comprises threads;
    where the first device comprises an axial length of between 5 mm and 30 mm;
    where the first section further comprises a diameter of between 5 mm and 30 mm;
    where the leading end comprises a scalloped edge and bevels; and
    where the lateral wall of the second section further comprises a plurality of fenestrations between the threads;
    f) attaching the first device to a driver by mating a distal end of the driver with the central aperture of the first device; and
    g) screwing the first device into the space using the driver until the joint-ward end of the first device forms a shape that substantially recreates a shape of the bone surface at an articulation area after implantation.

2. The method of claim 1, where the joint is selected from the group consisting of an acetabulofemoral joint, an acromioclavicular joint, a femoropatellar joint, a femorotibial joint, a glenohumeral joint, a humeroradial joint, a humeroulnar joint, an interphalangeal joint, a metacarpal joint, a radioulnar joint and a talocrural joint.

3. The method of claim 1, where the joint condition and disease is selected from the group consisting of arthroses, chondromalacia patella, isolated chondral defect, juvenile idiopathic arthritis, ligamentous deficiency arthroses, osteoarthritis, degenerative arthritis, degenerative joint disease, osteonecrosis, osteochondritis dissecans, patellar instability, post-ligamentous injury arthritis, post-meniscectomy arthritis, post-meniscectomy arthroses, post-traumatic arthritis, rheumatoid arthritis and septic arthritis.

4. The method of claim 1, where identifying the patient comprises diagnosing the patient with a joint condition and disease by performing one or more than one action selected from the group consisting of performing a physical examination, performing a non-invasive imaging examination and performing arthroscopy.

5. The method of claim 1, where identifying the patient comprises consulting patient records to determine if the patient has a joint condition or disease suitable for treatment by the method.

6. The method of claim 1, where accessing the joint is accomplished by arthroscopy or by an open surgical procedure.

7. The method of claim 1, where the surface of the bone comprises one or more than one abnormality, and where the method further comprises using a burr, or a suction shaver, or both a burr and a suction shaver to remove some or all of the one or more than one abnormality thereby creating a smoother articulation surface.

8. The method of claim 1, further comprising creating one or more than one vascular channel in the bone deep to the space using a drill bit guide positioned over the guidepin and a drill bit passed within the drill bit guide.

9. The method of claim 1, further comprising injecting a biological material in the first device.

10. The method of claim 1, further comprising placing an insert in the first device.

11. The method of claim 1, further comprising placing one or more than one additional device in the defect.

12. The method of claim 1, where the peripheral column comprises one or more than one notch.

13. The method of claim 1, where the lateral wall of the second section is generally cylindrical.

14. The method of claim 1, where the lateral wall of the second section is generally conical, tapering between the mating end and the leading end.

* * * * *